(12) United States Patent
Yunker

(10) Patent No.: US 7,533,428 B2
(45) Date of Patent: May 19, 2009

(54) MEDICAL BAG SUPPORT ASSEMBLY

(75) Inventor: David A. Yunker, Cicero, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 507 days.

(21) Appl. No.: 11/488,884

(22) Filed: Jul. 18, 2006

(65) Prior Publication Data

US 2008/0028525 A1   Feb. 7, 2008

(51) Int. Cl.
*A47C 21/00* (2006.01)
*A61G 13/10* (2006.01)
*A61B 6/04* (2006.01)
*F16M 11/08* (2006.01)

(52) U.S. Cl. ............... 5/601; 5/600; 5/503.1; 5/658; 378/209; 248/125.8

(58) Field of Classification Search .......... 5/601, 5/600, 658, 503.1; 378/209; 248/125.1, 248/125.8
See application file for complete search history.

(56) References Cited

U.S. PATENT DOCUMENTS

| | | | |
|---|---|---|---|
| 4,105,923 A | | 8/1978 | Hynes, Jr. |
| 4,225,104 A | * | 9/1980 | Larson .................... 248/125.8 |
| 4,262,872 A | * | 4/1981 | Kodet ...................... 248/311.3 |
| 4,600,209 A | * | 7/1986 | Kerr, Jr. ....................... 280/400 |
| 4,729,576 A | * | 3/1988 | Roach ......................... 280/493 |
| 4,886,237 A | * | 12/1989 | Dennis .................. 248/289.11 |
| 4,945,592 A | * | 8/1990 | Sims et al. ..................... 5/658 |
| 4,966,340 A | * | 10/1990 | Hunter ..................... 248/125.8 |
| 4,969,768 A | | 11/1990 | Young |
| 5,078,349 A | | 1/1992 | Smith |
| 5,094,418 A | * | 3/1992 | McBarnes et al. ......... 248/286.1 |
| 5,149,036 A | * | 9/1992 | Sheehan ..................... 248/215 |
| 5,187,824 A | | 2/1993 | Stryker |
| 5,236,213 A | * | 8/1993 | Trickett ..................... 280/304.1 |
| 5,292,094 A | * | 3/1994 | VanKuiken ............... 248/125.1 |
| 5,319,816 A | * | 6/1994 | Ruehl ............................. 5/600 |
| 5,344,169 A | * | 9/1994 | Pryor et al. ................. 280/79.3 |
| 5,355,539 A | * | 10/1994 | Boettger ...................... 5/503.1 |
| 5,366,191 A | * | 11/1994 | Bekanich .................. 248/125.1 |
| 5,407,163 A | | 4/1995 | Kramer et al. |
| 5,477,575 A | | 12/1995 | Lehne et al. |
| 5,588,166 A | * | 12/1996 | Burnett ........................ 5/503.1 |
| 5,619,763 A | | 4/1997 | Randolph et al. |
| 5,924,658 A | | 7/1999 | Shiery et al. |
| 5,987,670 A | * | 11/1999 | Sims et al. ...................... 5/600 |
| 6,016,594 A | | 1/2000 | Frey |
| 6,079,678 A | * | 6/2000 | Schott et al. ........... 248/229.15 |
| 6,094,760 A | | 8/2000 | Nonaka et al. |
| 6,138,302 A | | 10/2000 | Sashin et al. |
| 6,179,260 B1 | * | 1/2001 | Ohanian ................. 248/229.16 |
| 6,375,133 B1 | | 4/2002 | Morrow |
| 6,456,684 B1 | | 9/2002 | Mun et al. |

(Continued)

*Primary Examiner*—Robert G Santos
(74) *Attorney, Agent, or Firm*—Peter L. Kendall

(57) ABSTRACT

A medical support assembly for a moving pallet of a diagnostic imaging device is provided. The medical support assembly includes a support member having an elongate shaft defining a longitudinal axis and a transverse shaft mounted substantially orthogonal with respect to the support member. The medical support assembly further includes a mounting adapter assembly supported by an attachment bracket of the moving pallet, the mounting adapter assembly being removably mounted and configured to enable rotational movement of the support member upon a substantial impact to the support member.

24 Claims, 5 Drawing Sheets

U.S. PATENT DOCUMENTS

| | | | |
|---|---|---|---|
| 6,601,860 B2 * | 8/2003 | Potter | 280/47.34 |
| 6,672,788 B2 | 1/2004 | Hathaway | |
| 6,688,569 B1 * | 2/2004 | Weiss | 248/229.15 |
| 6,704,956 B2 * | 3/2004 | Riley et al. | 5/600 |
| 6,854,357 B2 | 2/2005 | Jager et al. | |
| 6,885,165 B2 | 4/2005 | Henley et al. | |
| 6,929,398 B1 | 8/2005 | Tybinkowski et al. | |
| 7,008,269 B2 * | 3/2006 | Riley et al. | 439/668 |
| 2007/0023587 A1 * | 2/2007 | Eggleston et al. | 248/98 |
| 2007/0176063 A1 * | 8/2007 | Heimbrock et al. | 248/176.1 |
| 2007/0267556 A1 * | 11/2007 | Herskovic | 248/218.4 |
| 2008/0028525 A1 * | 2/2008 | Yunker | 5/601 |
| 2008/0078902 A1 * | 4/2008 | Skoff | 248/227.3 |

* cited by examiner

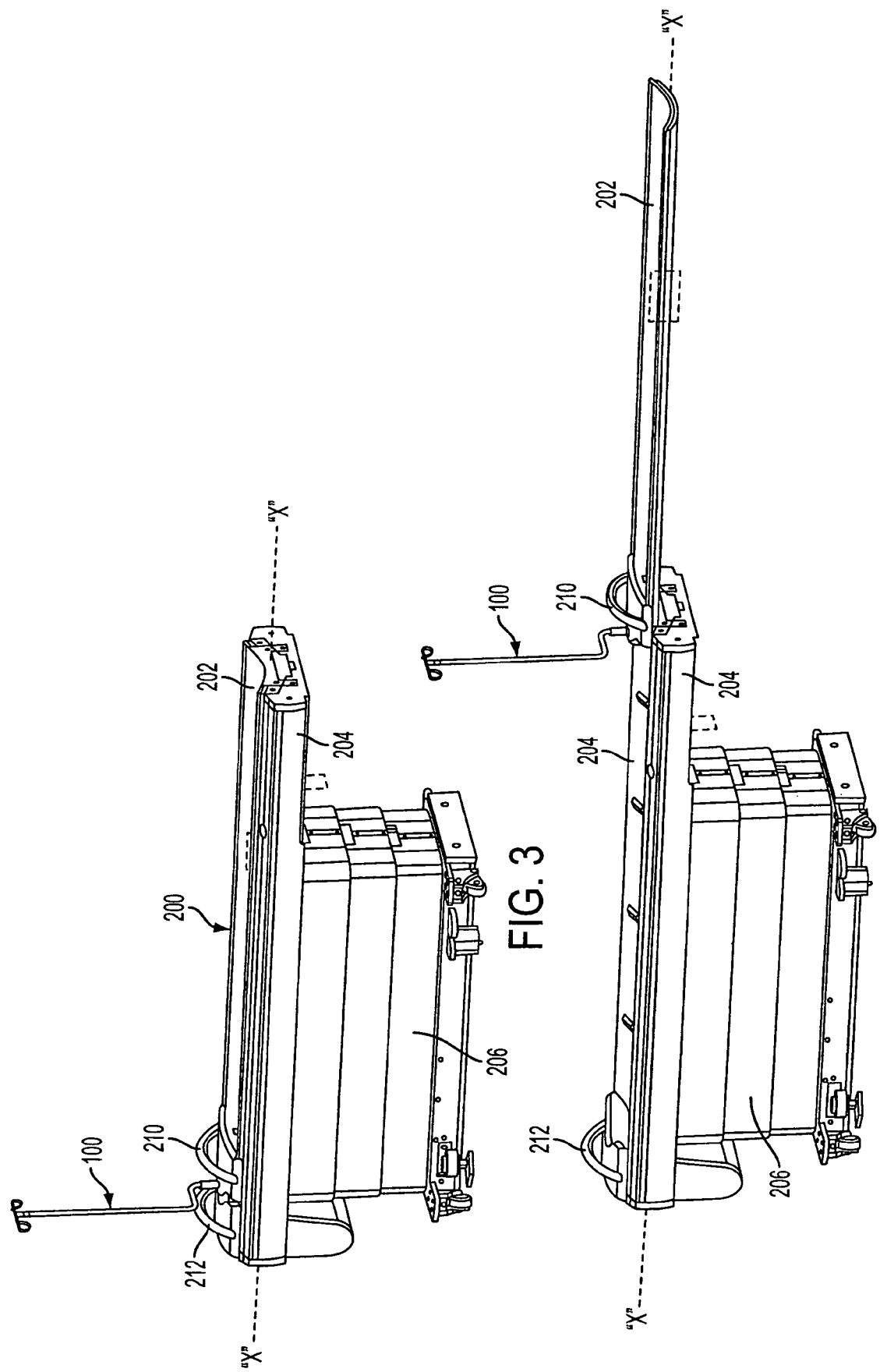

MEDICAL BAG SUPPORT ASSEMBLY

BACKGROUND

1. Technical Field

The present disclosure relates generally to a coupling and/or support mechanism for supporting at least a medical bag and, more particularly, to a medical support assembly for supporting at least an intravenous (IV) and/or IV bag on a patient pallet of a medical examination apparatus or diagnostic imaging device.

2. Description of Related Art

During the course of certain medical treatments and procedures, a patient may require intravenous fluids provided by an intravenous system having a bag or reservoir containing an intravenous fluid. The bag is typically supported on at least one support assembly, such as, for example, an IV pole. In general an IV pole includes a support stand having an elongated member attached thereto, and a plurality of hooks or loops arranged about the elongated member for supporting the bag of the intravenous system. It is beneficial that the IV pole be positioned adjacent to the patient and fully controlled at all times to ensure patient safety and comfort.

The bag is typically supported by one or a plurality of hooks arranged on the elongated member of the IV pole. The IV pole may be a separate, stand-alone unit, or the IV pole may be fixedly secured or attached to a patient pallet. In many applications, the IV pole permits the patient to be moved or transported when required without interrupting or disturbing delivery of the intravenous fluid. Thus, the IV pole is a commonly used device at hospitals and medical facilities. Examples of IV poles are described in U.S. Pat. No. 5,924,658 to Shiery et al.; U.S. Pat. No. 5,149,036 to Sheehan; and U.S. Pat. No. 5,094,418 to McBarnes, Jr. et al., the entire contents of each of which are hereby incorporated herein by reference.

Various arrangements for coupling an IV pole to a patient pallet are known in the prior art. U.S. Pat. No. 5,149,036 to Sheehan, for example, discloses an IV pole having a bracket and a U-shaped clamp member attached to the bracket, the bracket being attached to a patient pallet or bed such that the IV pole and the pallet act as an integral unit. However, the arrangements in the prior art are not suitable for use in a movable pallet such as the one commonly used in a medical diagnostic imaging device. That is, when diagnostic imaging is to be performed on patients requiring IV access, the use of IV poles presents a challenge since, typically, a medical diagnostic imaging device includes a movable pallet for moving the patient in and out of a gantry. Thus, a problem arises in easily moving patients in and out of the gantry when the patient is attached to an IV bag supported by the IV pole. It is desirable and often necessary that the IV pole be moved simultaneously with the patient without any relative movement between the patient and the IV pole.

With reference to FIGS. 1 and 2, a prior art medical diagnostic imaging device includes a pallet 10 including an IV pole assembly 12 having an IV pole 14 attached to pallet 10. As shown in FIG. 1, a patient "P" is positioned on pallet 10 for moving the patient "P" into a gantry 16 and adjacent at least one diagnostic imaging device 18 by an operator or technician "T". IV pole 14 supports a container or fluid bag 20 and tubing 22. IV pole 14 is attached to pallet 10 for movement in unison with pallet 10. IV pole 14 further includes hook members 24 for supporting fluid bag 20. IV pole 14 is attached to pallet 10 via a bracket member 26, wherein bracket member 26 engages a support rail 28 of pallet 10. In use, pallet 10 is moved along a horizontal plane towards gantry 16. As patient "P" is transported towards gantry 16, IV pole 14 moves in unison with pallet 10. However, a top portion of IV pole 14 may collide with overhead objects such as, for example, a Patient Positioning Management (PPM) device 30. Any contact of IV pole 14 with device 30, as pallet 10 is moved, may cause tubing 22 to become entangled, may cause disconnection of needles from the patient "P", may cause kinking of tubing 22, etc., thus disrupting delivery of IV fluid and causing patient discomfort, contamination, etc.

A possible solution has been to require extra personnel to guide the IV pole along with the pallet to ensure that the IV system remains intact and the patient remains safe and comfortable during the diagnostic imaging. However, this requires additional personnel and additional coordination between 2 or more personnel, including the technician "T".

Accordingly, there exists a need for an IV support mechanism for a movable pallet of a medical diagnostic imaging device which overcomes the problems and limitations of the prior art.

SUMMARY

The present disclosure relates to a medical support assembly for supporting at least an intravenous (IV) and/or IV bag on a patient pallet of a medical examination apparatus or diagnostic imaging device.

According to one aspect of the present disclosure, a medical support assembly for a moving pallet of a diagnostic imaging device is provided. The medical support assembly includes a support member having an elongate shaft defining a longitudinal axis and a transverse shaft mounted substantially orthogonal with respect to the support member. The medical support assembly further includes a mounting adapter assembly supported by an attachment bracket of the moving pallet, the mounting adapter assembly being removably mounted and configured to enable rotational movement of the support member upon a substantial impact to the support member.

According to another aspect of the present disclosure, a patient support system is provided. The patient support system includes a movable pallet for supporting a patient thereon and having an attachment bracket adjacent thereto, and a medical support assembly. The medical support assembly includes a support member having an elongate shaft defining a longitudinal axis and a transverse shaft mounted substantially orthogonal with respect to the support member; and a mounting adapter assembly supported by an attachment bracket of the moving pallet, the mounting adapter assembly being removably mounted and configured to enable rotational movement of the support member upon application of an axial force to the support member.

According to yet another aspect of the present disclosure, an IV support assembly is provided. The TV support assembly includes a support member having a crank mechanism and being in operable communication with a movable pallet of a diagnostic imaging device; a mounting adapter assembly in communication with the crank mechanism, the mounting adapter assembly being adapted for rotational movement in response to a predetermined axial force applied to the support member; a processor for controlling and effecting movement of the movable pallet; and a switch element in operable communication with the processor for enabling and disabling movement of the pallet. In operation, rotational movement of the mounting adapter assembly actuates the switch element to disable movement of the patient pallet.

Other features of the presently disclosed IV support assembly will become apparent from the following detailed description, taken in conjunction with the accompanying drawings, which illustrate, by way of example, the presently disclosed IV support assembly.

BRIEF DESCRIPTION OF THE DRAWINGS

The features of the presently disclosed IV support assembly will be described hereinbelow with reference to the figures, wherein:

FIG. 3 is a perspective view of an IV support assembly, according to an embodiment of the present disclosure, attached to a patient pallet assembly wherein a pallet of the patient pallet assembly is shown in a retracted condition;

FIG. 4 is a perspective view of the IV support assembly of FIG. 3, wherein the pallet of the patient pallet assembly is shown in an extended condition according to an embodiment of the present disclosure;

DETAILED DESCRIPTION

Figure 1:
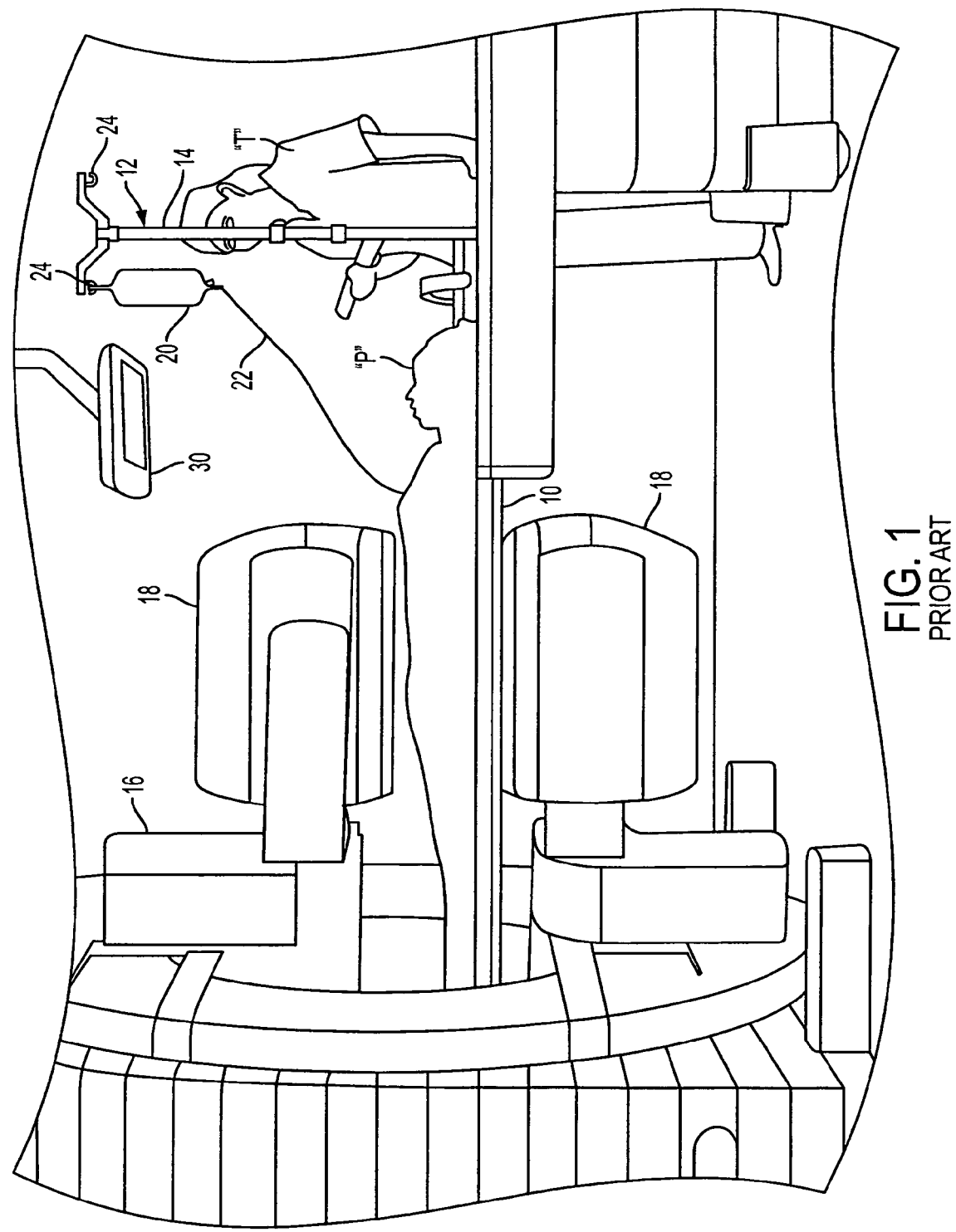
FIG. 1 is a schematic illustration of a medical diagnosis imaging device having an IV pole assembly attached thereto in accordance with the prior art.

Referring now to the drawing figures, wherein like references numerals identify identical or corresponding elements, various embodiments of the presently disclosed IV support mechanism will now be described in detail.

During medical imaging evaluations, a patient having an IV access is positioned horizontally on a pallet assembly 200, and is then mechanically moved into position within a gantry of a diagnostic imaging device. Typically, an IV support assembly moves in unison with pallet assembly 200. Although the description of the IV support assembly, as discussed herein, is in the context of medical diagnostic imaging devices, it should be understood that the present disclosure may also be applied in connection with other diagnostic applications, such as, for example, in applications where a patient connected to an IV needs to be moved or transported from one treatment area to another.

Figure 2:
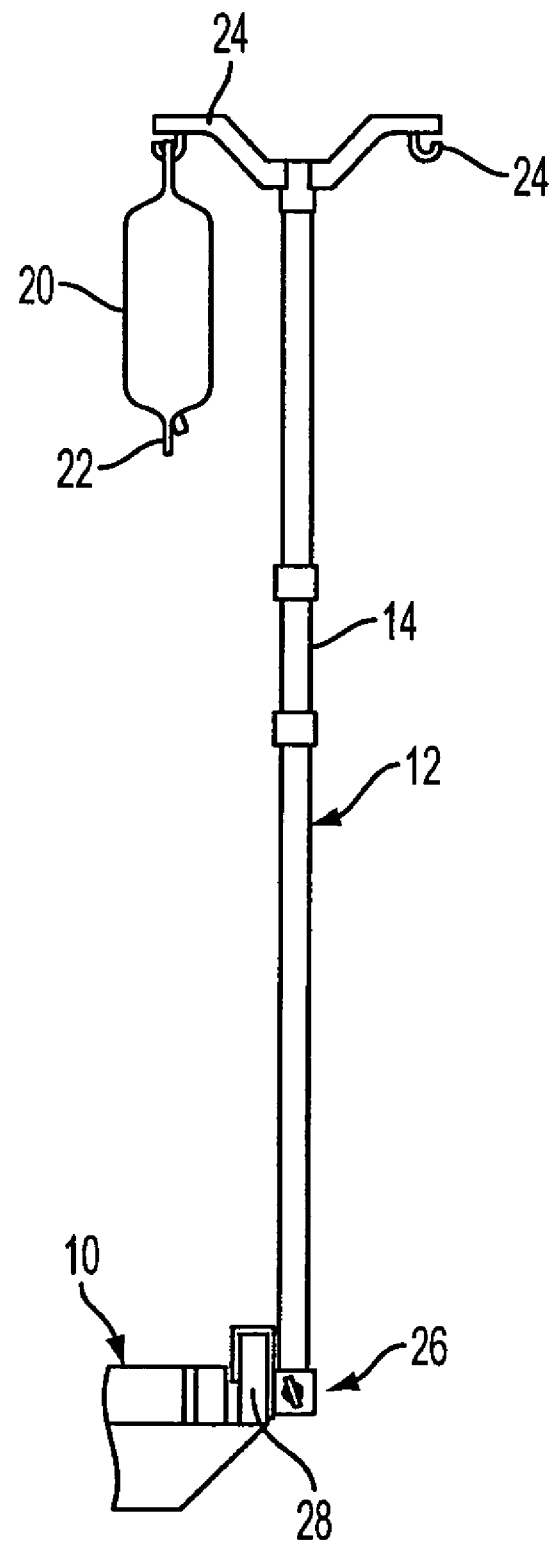
FIG. 2 is a front view of the prior art IV pole assembly shown in FIG. 1.

With initial reference to FIGS. 3 and 4, an IV support assembly 100, in accordance with an embodiment of the present disclosure, for use in connection with a patient handling system 200 of a medical diagnostic imaging device, is illustrated. Medical diagnostic imaging device may be configured for conducting, for example, and not limited to, tomographic, ultrasonographic, radiographic and fluoroscopic examinations. As will be discussed in greater detail below, IV support assembly 100 is adapted to engage and secure an IV pole 106 to a movable pallet 202 of patient handling system 200. IV pole 106 may support intravenous fluid bags 20 (see FIGS. 1 and 2), containers, monitors, infusion pumps, or the like. IV support assembly 100 is configured and adapted for rotational movement, wherein rotation of IV pole 106 beyond a threshold distance actuates a switch to discontinue axial movement of pallet 202, as will be discussed in greater detail below.

With continued reference to FIGS. 3 and 4, patient handling system 200 includes a patient pallet 202 for supporting a patient (not shown) thereon; a pallet support 204 for slidably receiving patient pallet 202; and a pedestal 206 for supporting pallet support 204 thereon. One suitable patient handling system 200 is disclosed in U.S. Pat. No. 5,619,763 to Randolph et al., the entire contents of which are incorporated herein by reference. Patient handling system 200 is configured to support an attachment bracket 208 (see FIG. 5) for receiving and supporting IV support assembly 100, in a manner described in detail hereinbelow. One suitable attachment bracket 208 may be the attachment bracket disclosed in U.S. Pat. No. 6,929,398 to Tybinkowski et al., the entire contents of which are incorporated herein by reference.

Patient handling system 200 further includes a processor or the like (not shown) associated with an adjusting mechanism (not shown) for controlling the positioning (i.e. horizontal and/or vertical positioning) of patient pallet 202. In addition, handles 210 and 212 are positioned at a proximal portion of patient pallet 202 and pallet support 204, respectively. Handles 210 and 212 are adapted for aiding the technician "T" and/or the patient "P" during a diagnostic imaging application. As illustrated in FIG. 4, patient pallet 202 is adapted for slidable movement relative to pallet support 204 and pedestal 206, for positioning patient pallet 202 into a gantry (not shown) of a medical imaging device. In particular, patient pallet 202 is adapted for sliding, axial movement, along a longitudinal "X" axis, between a first un-extended position and a second extended position, for positioning the patient "P" within the gantry of the medical imaging device. Moreover, IV support assembly 100 is adapted to move in unison with patient pallet 202, in a manner described in detail hereinbelow.

Figure 5:
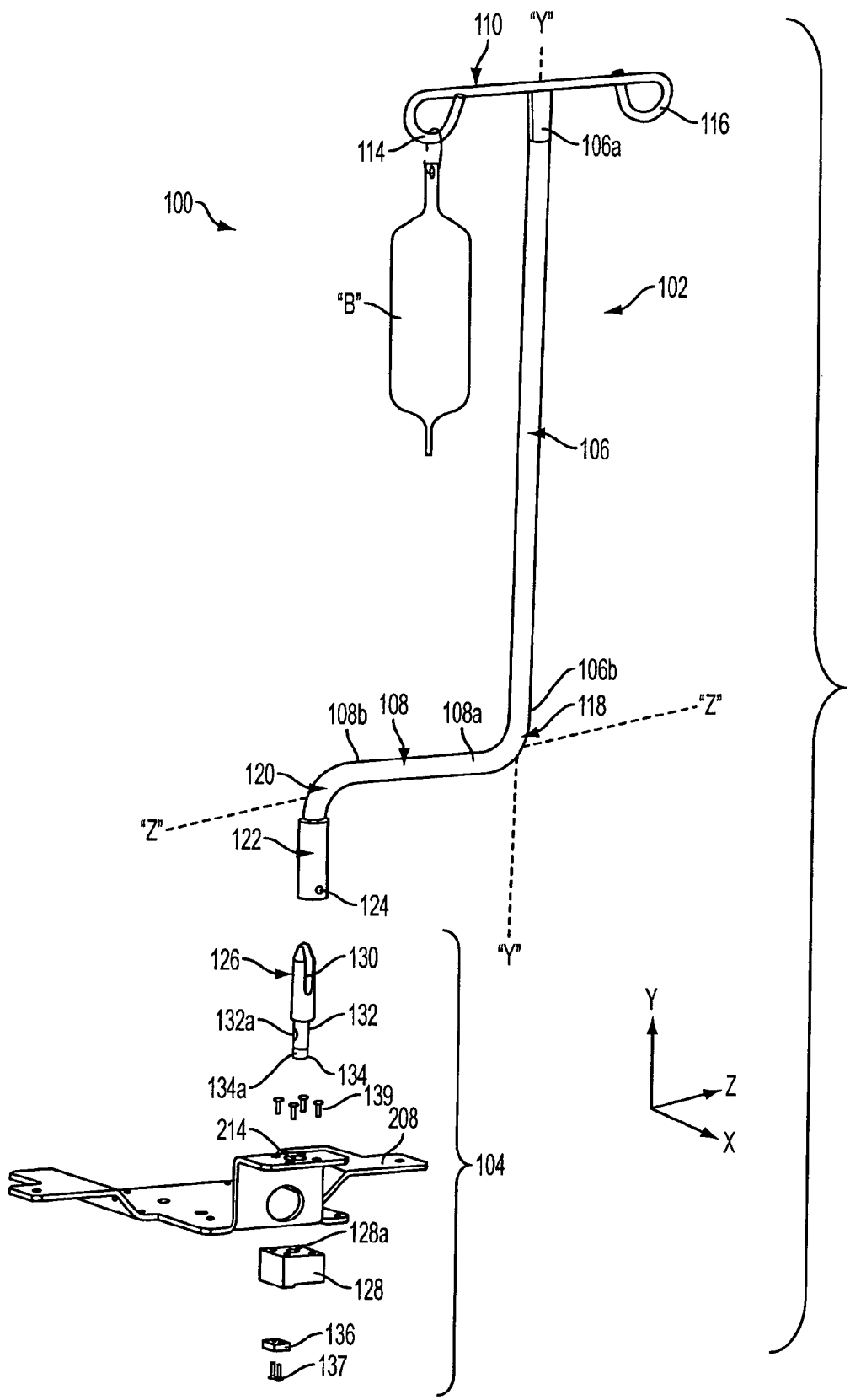
FIG. 5 is an exploded isolated perspective view of the IV support assembly of FIG. 3 according to an embodiment of the present disclosure.
Figure 6:
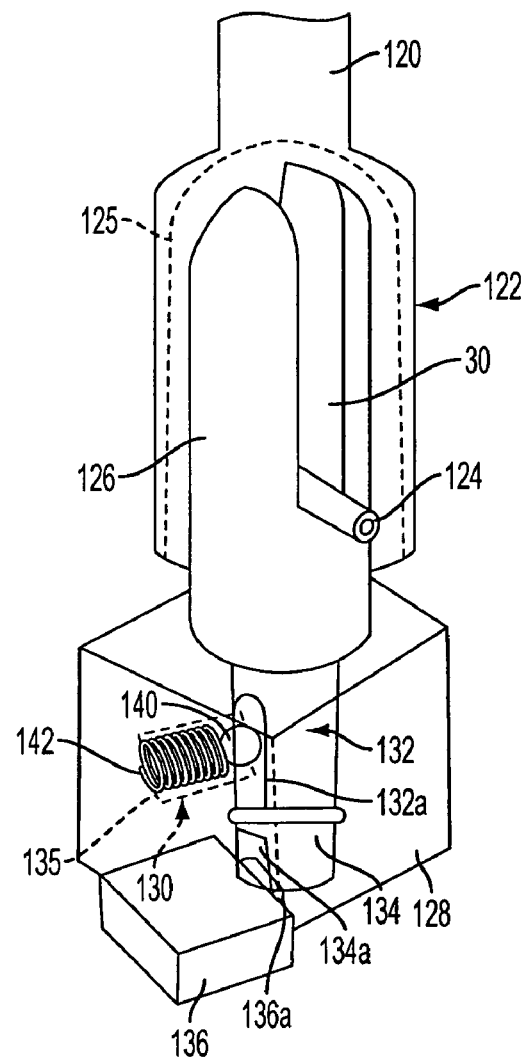
FIG. 6 is an enlarged perspective view of a mounting adapter assembly of the IV support assembly of FIG. 3 according to an embodiment of the present disclosure.
Figure 7:
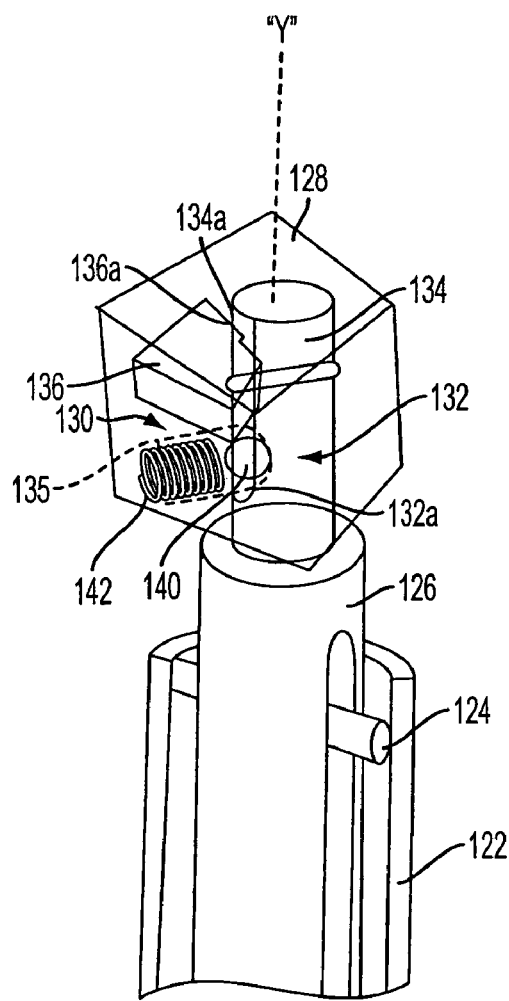
FIG. 7 is an inverted view of FIG. 6 according to an embodiment of the present disclosure.

Turning now to FIGS. 5-7, in conjunction with FIGS. 3 and 4, IV support assembly 100 includes a support member 102 operatively connectable, supportable and rotatable on a mounting adapter assembly 104. Support member 102 includes an elongate shaft 106 defining a longitudinal "Y" axis and a transverse shaft 108 oriented in a substantially normal direction, along a "Z" axis, with respect to the longitudinal "Y" axis of elongate shaft 106. Support member 102 includes a first elbow 118 interconnecting a lower end portion 106b of elongate shaft 106 and a first end 108a of transverse shaft 108. Support member 102 of IV support assembly 100 further includes a support bar 110 mounted to an upper end portion 106a of elongate shaft 106. Support bar 110 may include at least one loop or hook member 114, 116, provided at opposed ends thereof, for supporting, for example, an IV bag "B" or the like.

Transverse shaft 108 includes first end 108a connected to first elbow 118 and a second end 108b connected to a second elbow 120. Second elbow 120 is configured for supporting and orienting a socket member 122 in a direction substantially parallel to the longitudinal "Y" axis. Socket member 122 facilitates selective attachment of IV support assembly 100 to mounting adapter assembly 104. Socket member 122 includes a pin 124 positioned transversely across a bore or recess 125 (shown in hidden lines in FIG. 6) defined within socket member 122.

With continued reference to FIG. 5, mounting adapter assembly 104 includes a boss or pin member 126 having an open ended slot 130 formed therein. Slot 130 is dimensioned and configured to accommodate pin 124 of socket member 122. Pin member 126 further includes a reduced diameter tubular extension 132 extending therefrom and a collar 134 disposed at an end of tubular extension 132. Tubular extension 132 includes a detent groove 132a formed therein and collar 134 having a flat portion 134a formed thereon. Tubular extension 132 is dimensioned and configured for projecting through an opening 214 formed in attachment bracket 208 of patient handling system 200 and into a receptacle housing 128 supported beneath bracket 208. As so arranged, as support member 102 is rotated about socket member 122, pin 124 of socket member 122 transmits rotation to pin member 126, in a manner which will be described in greater detail hereinbelow.

With continued reference to FIG. 5-7, receptacle housing 128 is mounted to attachment bracket 212, via screws 139. Receptacle housing 128 includes an opening 128a formed therein for receiving tubular extension 132 of pin member 126 therein. Opening 128a of receptacle housing 128 is in registration with opening 214 of attachment bracket 208. A switch element 136 is attached to receptacle housing 128 by screws 137. Switch element 136 is operably connected to the processor of patient handling system 200 and functions to transmit a signal to the processor upon rotation of pin member 126 beyond a predetermined threshold distance. Switch element 136 includes a plunger 136a extending therefrom. When flat portion 134a of collar 134 of pin member 126 is in registration with plunger 136a, plunger 136a is in an extended or projected condition. When pin member 126 is rotated such that flat portion 134a of collar 134 is out of registration with plunger 136a, an outer surface of collar 134 presses plunger inward to activate switch element 136. It is contemplated that plunger 136a may be biased to an extended condition. It is further contemplated that switch element 136 may be electrically activated as a result of an electrical connection with a contact pad provided on pin member 126, or activated via magnetic/inductive/capacitive elements provided on switch element 136 and/or pin member 126, etc.

In operation, when pin member 126 has been rotated, from a position where plunger 136a of switch element 136 is in registration with flat surface 134a of collar 134 to a position where plunger 136a of switch element 136 is out of registration with flat surface 134a of collar 134, plunger 136a is pushed into switch element 136 as a result of a camming action between plunger 136a and an outer surface of collar 134 of pin member 126. When plunger 136a is depressed, a signal is transmitted to the processor of patient handling system 200. The transmitted signal is received by the processor which in turn causes patient pallet 202 to stop moving relative to pallet support 204.

Turning now to FIGS. 6 and 7, receptacle housing 128 includes a ball detent feature 130, such as, for example, a spring-loaded ball operatively associated with opening 128a of receptacle housing 128. Ball detent feature 130 includes at least one ball 140 and biasing means, such as, spring 142 for biasing ball 140 towards and at least partially into opening 128a of receptacle housing 128. Ball 140 may be constructed from stainless steel and the like, but may also be made from any other suitable material. Ball 140 is reciprocally retained in a bore 135 formed in receptacle housing 128. In this particular embodiment, bore 135 may include a smaller diameter opening so as to prevent ball 140 from escaping therefrom. Spring 142 exerts an axial spring-loading force on ball 140 and biases ball 140 at least partially into opening 128a of receptacle housing 128.

As seen in FIGS. 6 and 7, when detent groove 132a of pin member 126 is in a first position within receptacle housing 128, at least a portion of ball 140 projects or extends into detent groove 132a. The partial positioning of ball 140 in detent groove 132a of pin member 126 inhibits rotation of pin member 126 relative to receptacle housing 128 and thus inhibits rotation of support member 102 about socket member 122. As such, support member 102 is maintained in a relatively fixed position. However, when a rotational force is exerted on pin member 126 which is sufficiently great so as to overcome the bias of spring 142, ball 140 is pushed into bore 135, as a result of a camming action between ball 140 and an outer surface of tubular extension 132 of pin member 126. When ball 140 has been pushed into bore 135, pin member 126 may rotate within opening 128a of receptacle housing 128. It is noted that the magnitude of the rotational force is a function of the geometry of support member 102 and of the spring constant of spring 142.

IV support assembly 100 is initially mounted to mounting adapter assembly 104 such that transverse shaft 108 of support member 102 is oriented in a direction orthogonal to the "X and Y" axes. In this manner, in operation, any impact on support member 102, resulting from movement of patient pallet 202 of patient pallet assembly 200, will necessarily be in a direction which is substantially parallel to the longitudinal "X" axis or the axis of movement of patient pallet 202. Thus, socket member 122 and transverse shaft 108 function as a crank for changing the axial motion of support member 102 along the longitudinal "X" axis into rotational motion about pin member 126. In particular, during movement of patient pallet 202 in an axial direction along the longitudinal "X" axis, when support member 102 comes into contact with an overhead object, such as, for example, a patient positioning management system, a force is created on support member 102 in a direction parallel to the "X" axis and parallel to the axial direction of movement of patent pallet 202. This axial force is transmitted to socket member 122 as a torsional force created by transverse shaft 108. In turn, pin 124 of socket member 122 engages pin slot 130 of pin member 126 for transmitting the torsional force thereto.

When the torsional force transmitted to pin member 126 is sufficient to cause the outer surface of tubular extension 132 to cam against ball 140 and push ball 140, against the bias of spring 142, into bore 135, thereby disengaging ball 140 from detent groove 132a of tubular extension and causing support member 102 to be rotated about the longitudinal axis of pin member 126. Rotation of pin member 126 causes flat portion 134a of collar 134 to move out of registration with plunger 136a of switch element 136. As flat portion 134a of collar 134 is rotated out of registration with plunger 136a of switch element 136 an outer surface of collar 134 functions as a cam to actuate switch element 136. Actuation of switch element 136 transmits a signal to a processor which stops the axial movement of patient pallet 202. Alternatively, switch element 136 may activate an alarm alerting the technician "T" that support member 102 has come into contact with an object.

Thus whenever the rotation of pin member 126 exceeds a predetermined limit, flat portion 134a of collar 134 of pin member 126 actuates switch element 136 to alert the processor to stop the axial advancement of patient pallet 202.

It will be understood that numerous modifications and changes in form and detail are contemplated herein, and the scope of the present disclosure is not limited thereby. For example, it is contemplated that numerous other configuration of the IV support assembly 100 may be used, and the components of the IV support assembly 100 may be selected from numerous components other than those specifically disclosed without departing from the scope of the disclosure as defined in the appended claims. Therefore, the above description should not be construed as limiting the disclosed IV support assembly 100 but merely as exemplifications of the various embodiments thereof. Those skilled in the art will envision numerous modifications within the scope of the present disclosure as defined by the claims appended hereto.

In short, it is the Applicant's intention that the scope of the patent issuing herefrom will be limited only by the scope of the appended claims. Having thus described the invention with the details and particularity required by the patent laws, what is claimed and desired protected is set forth in the appended claims.

What is claimed is:

1. A medical support assembly for a moving pallet of a diagnostic imaging device, the assembly comprising:
   a support member having an elongate shaft defining a longitudinal axis and a transverse shaft mounted substantially orthogonal with respect to the support member;
   a mounting adapter assembly supported by an attachment bracket of the moving pallet, the mounting adapter assembly being removably mounted and configured to enable rotational movement of the support member upon a substantial impact to the support member; and
   a processor for effecting movement of the pallet, wherein a switch element is actuatable by said rotational movement of the support member, and further wherein said switch element is in operable communication with the processor of the patient pallet.

2. The medical support assembly as recited in claim 1, wherein the support member includes at least one hook disposed in a first end thereof for receiving at least one IV system.

3. The medical support assembly as recited in claim 2, wherein the IV system is selected from a group consisting of at least one of an IV fluid bag, a container, a monitor, and an infusion pump.

4. The medical support assembly as recited in claim 1, wherein actuation of the switch element enables and disables movement of the patent pallet.

5. The medical support assembly as recited in claim 1, wherein the mounting adapter assembly includes:
   a pin member having a reduced diameter tubular extension; and
   a housing including at least one opening formed therein for receiving the reduced diameter tubular extension of the pin member,
   wherein the pin member is adapted for rotational movement relative to the housing between a first position and a second position for actuating the switch element.

6. The medical support assembly as recited in claim 5, further comprising a socket member defining a mounting recess and being fixedly positioned at an end portion of the support member, the socket member having a pin positioned transversely across the mounting recess.

7. The medical support assembly as recited in claim 6, wherein the pin member defines an open ended pin slot for engaging the pin of the socket member.

8. The medical support assembly as recited in claim 7, wherein the pin member is selectively engageable with the socket member.

9. The medical support assembly as recited in claim 5, further comprising a detent feature positioned within the housing for inhibiting rotation of the support member.

10. The medical support assembly as recited in claim 9, wherein the detent feature includes at least one ball and at least one biasing means.

11. The medical support assembly as recited in claim 9, wherein the pin member includes a detent groove for receiving at least a portion of the detent feature therein.

12. The medical support assembly as recited in claim 1, wherein the substantial impact results from the motion of the pallet.

13. A patient support system comprising:
   a movable pallet for supporting a patient thereon and having an attachment bracket adjacent thereto; and
   a medical support assembly including
   a support member having an elongate shaft defining a longitudinal axis and a transverse shaft mounted substantially orthogonal with respect to the support member; and
   a mounting adapter assembly support by an attachment bracket of the moving pallet, the mounting adapter assembly being removably mounted and configured to enable rotational movement of the support member upon application of an axial force to the support member
   wherein the movable pallet is operably connected to a processor and a switch element effecting movement of the pallet, and
   wherein the switch element is actuated by said rotational movement.

14. The patient support system as recited in claim 13, wherein the axial force results from the motion of the pallet.

15. The patient support system as recited in claim 13, wherein actuation of a switch element enables and disables movement of the pallet.

16. The patient support system as recited in claim 13, wherein the support member includes a socket member defining an opening having a pin positioned transversely thereacross; and wherein the mounting adapter includes a pin member having a pin slot formed therein for selectively engaging the pin of the socket member.

17. The patient support system as recited in claim 16, wherein the pin member is adapted for rotational movement between a first position and a second position in response to the axial force to the support member.

18. The patient support system as recited in claim 17, wherein a switch member is actuated when the pin member is in the second position, and further therein the switch element is in operative communication with a processor of the movable pallet.

19. The patient support system as recited in claim 16, wherein the mounting adapter further includes a detent feature in operative communication with the pin member for inhibiting the rotational movement of the support member.

20. The patient support system as recited in claim 19, therein the detent feature includes at least one spring loaded ball for biasing the pin member in the first position.

21. An IV support assembly, comprising:
   a support member having a crank mechanism and being in operable communication with a movable pallet of a diagnostic imaging device;
   a mounting adapter assembly in communication with the crank mechanism, the mounting adapter assembly being adapted for rotational movement in response to a predetermined axial force applied to the support member;
   a processor for controlling and effecting movement of the movable pallet; and
   a switch element in operable communication with the processor for enabling and disabling movement of the pallet;
   wherein rotational movement of the mounting adapter assembly actuates the switch element to disable movement of the patient pallet.

22. The IV support assembly as recited in claim 21, wherein the mounting adapter assembly includes:
   a pin member having a reduced diameter section; and
   a housing including at least one opening formed therein for receiving the reduced diameter section of the pin member, wherein the pin member is adapted for rotational movement relative to the housing between a first position and a second position for actuating the switch element.

23. The IV support assembly as recited in claim 21, wherein the reduced diameter portion includes a cam surface for engaging a portion of the switch element upon rotation of the pin member.

24. The IV support assembly as recited in claim 22, wherein the mounting adapter assembly further includes a detent feature positioned within the housing, the detent feature having a spring loaded ball operably engageable with the pin member for inhibiting the rotational movement of the pin member.

* * * * *